United States Patent [19]

Drewlow

[11] Patent Number: Plant 6,396

[45] Date of Patent: Nov. 15, 1988

[54] STREPTOCARPUS PLANT NAMED ARIADNE

[75] Inventor: Lyndon W. Drewlow, Ashtabula, Ohio

[73] Assignee: Mikkelsens, Inc., Ashtabula, Ohio

[21] Appl. No.: 9,376

[22] Filed: Jan. 30, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A Streptocarpus plant named Ariadne characterized by its compact growth habit, white flowers with magenta streaking on lower petals; floriferous habit, early flowering, tolerance to low light and high temperature, relatively small leaves, and by its long lasting and non-shattering flowers.

1 Drawing Sheet

The present invention relates to a new and distinct cultivar of Streptocarpus plant, botanically known as *Streptocarpus×hybridus,* and known by the cultivar name Ariadne. Ariadne was developed by me through controlled breeding by crossing Mikkelsen Seedling 82-1419-36 (seed parent)×Mikkelsen Seedling 82-1096-3 (pollen parent).

Asexual reproduction by me by leaf cuttings has shown that the unique features of Ariadne are stabilized and are reproduced true to type in successive propagations.

The following characteristics distinguish the new Streptocarpus from both its parent varieties and other cultivated Streptocarpus of this type known and used in the floriculture industry:

1. Ariadne is characterized by numerous short leaves in a rosette form instead of one large leaf that characterizes many older Streptocarpus cultivars. This results in a cluster of flowers in the middle of green foliage making an attractive 10 cm flowering plant.

2. Ariadne has similar flower size to Athena (not patented), is larger than Pegasus and Muse but not as large as the flowers of Achilles and Ulyssus. Pegasus, Muse, Achilles and Ulyssus are disclosed in pending applications, as in the cultivar Orion referred to below.

3. Ariadne's flower has a distinct yellow throat with magenta streaking from it onto the white lower petals, while Athena has a magenta throat with few streaks extending into the white lower petals.

4. The plant height and width of Ariadne are similar to Muse and Orion; smaller than Achilles and Ulyssus, but larger than Pegasus.

5. Ariadne is fast to propagate from leaf cuttings, producing numerous plantlets in 8 to 10 weeks depending on the time of the year. Also it is quick to flower from a well rooted plant out of a 72 cell pack. A well developed flowering plant can be obtained in 6 to 8 weeks.

6. Ariadne is very floriferous and has an average of 6 blooms per flower stalk compared to 5 for Achilles, 4 for Athena, and 3 for Ulyssus and Orion.

7. Flowers are long lasting, non-shattering, and the leaves are small and pliable, thus making this cultivar easy to ship.

8. Leaves of Ariadne are not as large as Athena, Ulyssus and Achilles; similar to Orion, and larger than Pegasus and Muse.

9. Ariadne has shown the ability to flower both under the lower light conditions of winter (December to February) and the higher temperatures of summer (July to September) without ever going out of bloom under greenhouse conditions.

10. Ariadne has also shown the ability to tolerate watering with 40° F. water without foliar spotting, and to tolerate fairly high light levels in summer without leaf bronzing.

The accompanying color photograph illustrates in perspective view the overall appearance of Ariadne, with colors being as true as it is reasonably possible to obtain in a color reproduction of this type.

The following is a detailed description of my new Streptocarpus cultivar based on plants produced under commercial practices in the greenhouses of Mikkelsens Inc., Ashtabula, Ohio. Color references are made to The Royal Horticultural Society Colour Chart (R.H.S.), except where general colors of ordinary dictionary significance are used.

Classification:

*Botanical.*—*Streptocarpus×hybridus,* cv. Ariadne.

Parentage: Controlled cross between Mikkelsen seedling 82-1419-36 and Mikkelsen seedling 82-1096-3.

Propagation:

A. *Type cutting.*—Leaf.

B. *Time to develop plantlets.*—Summer: 8 weeks at 20° C.; Winter: 10 weeks at 20° C.

C. *Rooting habit.*—Numerous, fine, fibrous.

Plant description:

A. *Form.*—Leaves are rosette, extending from a crown at the soil line. Leaves form all around the plant and produce a symmetrical plant with numerous bloom stalks in the center of the plant.

B. *Habit of growth.*—Vigorous, very free flowering, never going out of bloom once it starts blooming under greenhouse conditions. Leaves elliptical in shape, flower stalks from midrib of leaves, and flowers carried above foliage.

C. *Height from soil line.*—15 to 18 cm at maturity to top of blooms.

D. *Spread.*—35 to 40 cm at maturity. Leaf Size: 20 to 25 cm in length and 8 to 10 cm in width at the widest point; leaf size can very greatly with cultural conditions. Quantity: Mature may have more than 15 leaves. Leaf Shape: Elliptical. Texture: Lower surface rugose with veins protruding and pubescent; upper surface rugose and pubescent. Margin: Finely crenate. Color: Young foliage top side 137C; under side 145D. Mature foliage top side 137B; under side 139C. Ribs and veins: Pinnate. Rib and vein color: 146C. Leaf tips: Obtuse. Leaf base: Acute.

Flowering description:

Flowers open one at a time on the individual flower stalks.

A. *Fully expanded.*—50 to 52 mm.

B. *Stem.*—Single, green in color, round, variable in length, slightly pubescent; several from a leaf midrib.

C. *Form.*—Funnel shaped with calyx 5 parted with no tube; corolla cylindrical with 5 lobes, lobes orbicular to ovate with 2 upper petals slightly smaller than the 3 bottom petals. Open flowers appear flat.

D. *Flower bud description.*—Immature bud hangs downward, raising as it matures. At maturity bud is 22 to 25 mm long with 5 green calyx folded over the basal end.

E. *Flowers borne.*—In clusters of 5 to 6 flowers per flower stalk, with 6 the most common, on a mature plant carried above the foliage. Pedicels of the various flowers in the inflorescence vary in length.

F. *Quantity of flowers.*—Mature plant can have more than 15 flower stalks open with up to 6 flowers per stalk.

G. *Permanence.*—10 days or longer.

Color:

A. *Tonality from a distance.*—White with magenta streaking from the throat into the lower 3 petals with yellow in the throat.

B. *Upper surface of petals.*—155C streaked with 74A extending from throat to lower 3 petals.

C. *Under surface of petals.*—155C.

D. *Throat.*—3B with 74A streaking.

E. *Discoloration.*—Both yellow and magenta fade to lighter shades as flower ages.

Petals:

A. *Texture.*—Satin.

B. *Appearance.*—Individual lobed with entire margins, top 2 petals are reflexed and smaller than the bottom petals which are flat.

C. *Arrangement.*—Regularly united into an almost circular shape.

D. *Persistence.*—10 days or longer. Remain on plant in dry form until picked.

E. *Fragrance.*—None.

Reproductive Organs:

A. *Stamens.*—2 fertile, interconnected; 2 sterile, very small. Anther shape: 2 fertile, interconnected and flat. Anther color: white. Filament: 2 fertile are free standing for 6 mm and are white in color. Pollen color: white.

B. *Pistils.*—Stigma shape: flattened with reflex tips. Stigma color: white. Stigma size: 3 mm across. Style color: white. Style size: 5 mm. Ovaries: numerous, 10–12 mm on a receptive pistil, purplish.

Disease resistance: No disease problems to date.

Other important characteristics: Compact growth habit combined with an average of 6 flowers per bloom stalk that are carried above the foliage make Ariadne suitable for 10 cm pot plant production year round. Its early bloom, small leaves, and long lasting, non-shattering flowers further enhance this cultivar. Lack of major disease problems make for a trouble free crop.

I claim:

1. A new and distinct cultivar of Streptocarpus plant named Ariadne, as identified and described, and particularly characterized by its compact growth habit, white flowers with magenta streaking on lower petals; floriferous habit, early flowering, tolerance to low light and high temperature, relatively small leaves, and by its long lasting and non-shattering flowers.

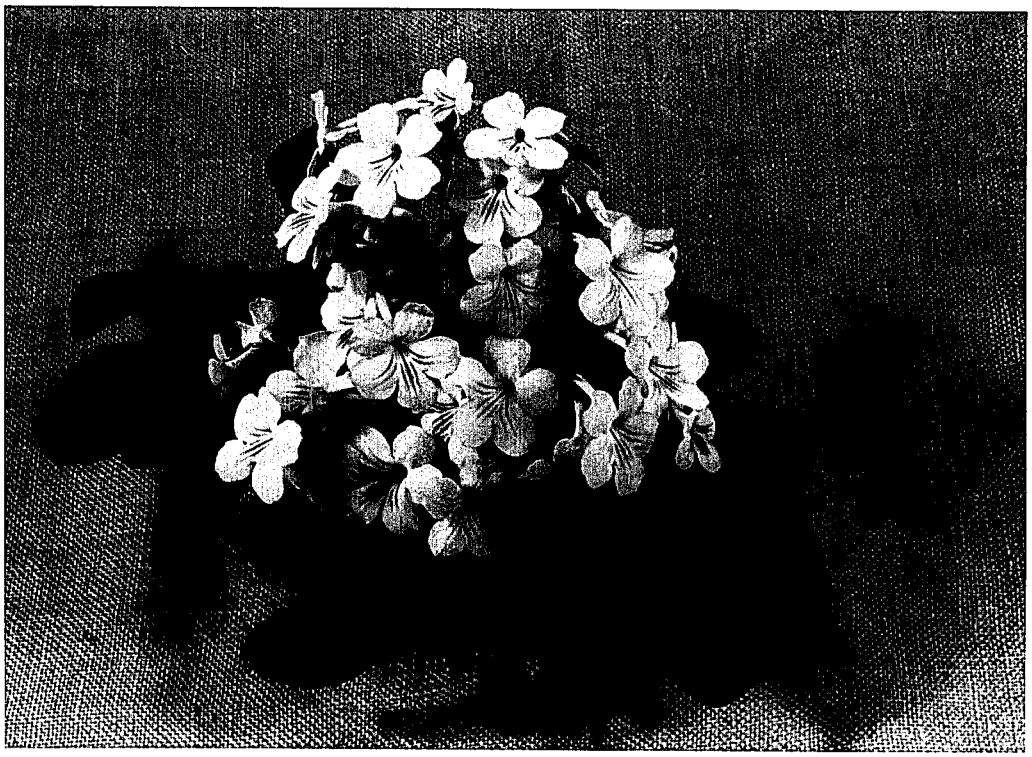

* * * * *